United States Patent
Watrelot et al.

(10) Patent No.: US 6,524,309 B1
(45) Date of Patent: Feb. 25, 2003

(54) BIPOLAR FORCEPS FOR CONDUCTING A PELVISCOPY

(75) Inventors: Antoine Watrelot, Lyons (FR); Thierry Loubens, Saint Didier au Mont d'Or (FR)

(73) Assignee: Soprane, Lyons (FR)

( * ) Notice: Subject to any disclaimer, the term of this patent is extended or adjusted under 35 U.S.C. 154(b) by 0 days.

(21) Appl. No.: 09/937,712

(22) PCT Filed: Feb. 22, 2000

(86) PCT No.: PCT/FR00/00439
§ 371 (c)(1),
(2), (4) Date: Nov. 30, 2001

(87) PCT Pub. No.: WO00/57802
PCT Pub. Date: Oct. 5, 2000

(30) Foreign Application Priority Data

Mar. 31, 1999 (FR) .............................................. 99 04223

(51) Int. Cl.[7] .............................................. A61B 18/18
(52) U.S. Cl. .............................. 606/51; 606/50; 606/52
(58) Field of Search .............................. 606/41, 45, 46, 606/48–52

(56) References Cited

U.S. PATENT DOCUMENTS

| | | | | |
|---|---|---|---|---|
| 3,920,021 A | * | 11/1975 | Hiltebrandt | 606/50 |
| 4,003,380 A | * | 1/1977 | Wien | 606/51 |
| 4,005,714 A | * | 2/1977 | Hiltebrandt | 606/51 |
| 4,016,881 A | * | 4/1977 | Rioux et al. | 606/42 |
| 4,054,143 A | * | 10/1977 | Bauer | 606/52 |
| 4,418,692 A | * | 12/1983 | Guay | 606/42 |
| 4,819,633 A | * | 4/1989 | Bauer et al. | 606/52 |
| 5,242,458 A | | 9/1993 | Bendel et al. | |
| 5,258,006 A | * | 11/1993 | Rydell et al. | 606/205 |
| 5,683,388 A | * | 11/1997 | Slater | 600/564 |

FOREIGN PATENT DOCUMENTS

EP 0 589 555 A1 3/1994

* cited by examiner

Primary Examiner—Michael Peffley
(74) Attorney, Agent, or Firm—Young & Thompson

(57) ABSTRACT

A bipolar forceps for conducting a pelviscopy comprising a pair of blades (2) that are made from a form-memorizing alloy and are partially covered by a plastic sheath (4) so that they can be fixed inside a tube (6). Each blade (2) has a non-sheathed end (5) with a curved profile which can become elastically deformed when the blades are moved in a longitudinal direction inside a guide (12) having a low internal diameter, in addition to comprising a cylindrical support (10) enabling the pair of blades (2) to be connected on the guide (12) and brought back into a specific position with the aid of elastic elements (13). Elements (11) are also provided for enabling the pair of blades (2) to be connected to a voltage source (3) so that each blade can function according to an electrode in order to enable coagulation of tissues.

5 Claims, 7 Drawing Sheets

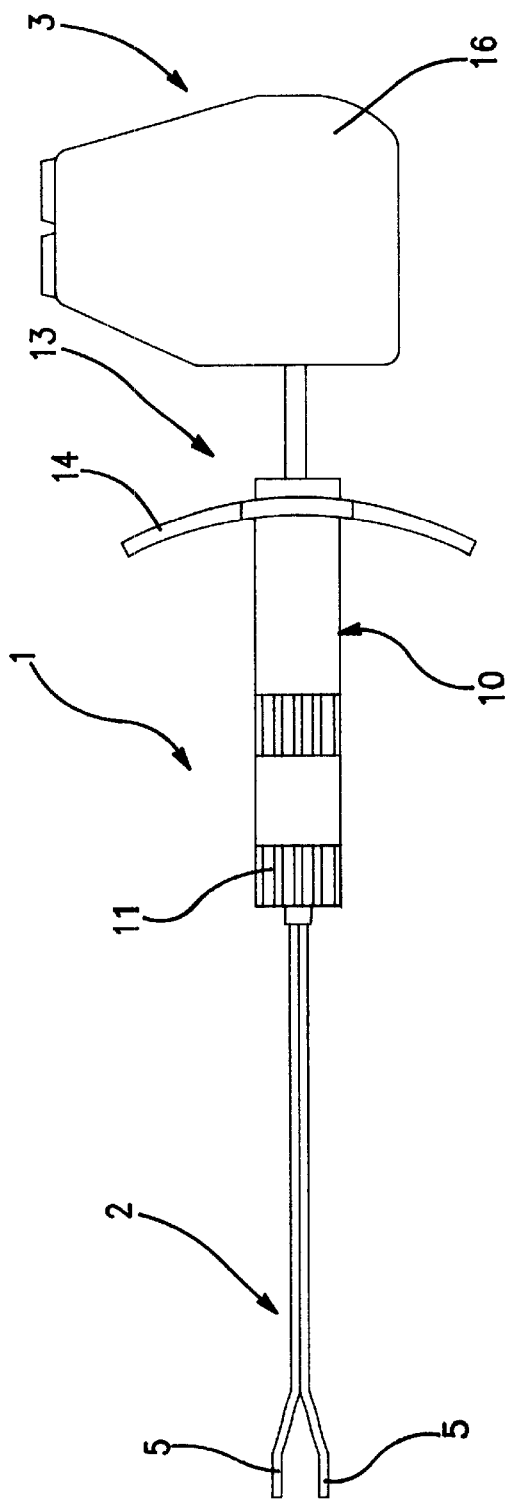
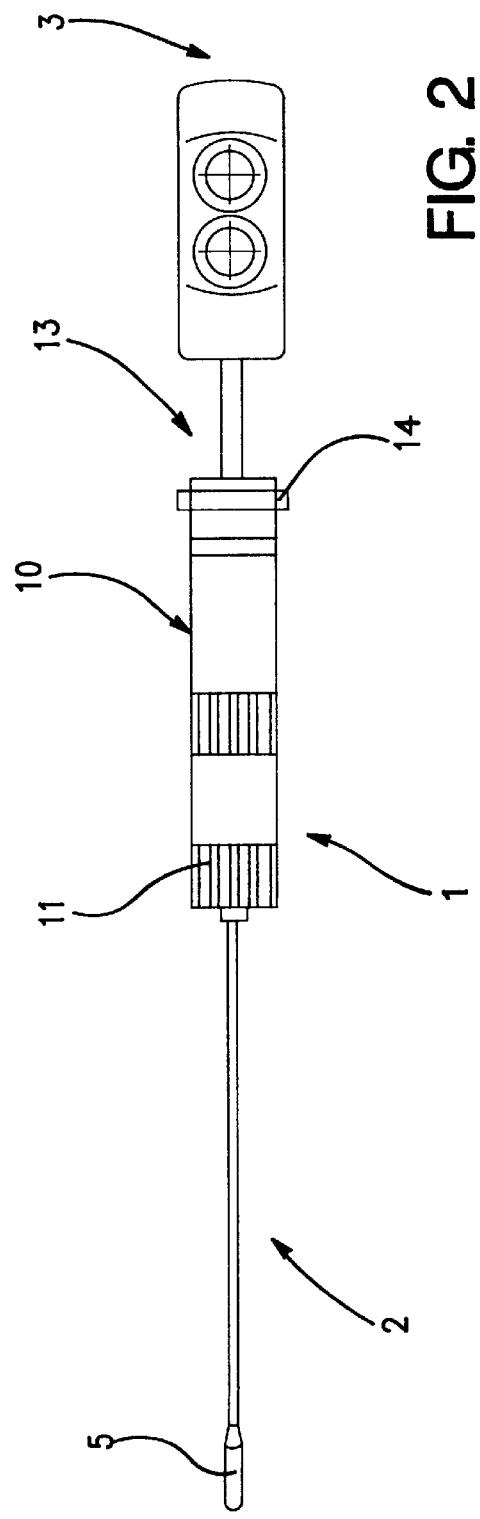

BIPOLAR FORCEPS FOR CONDUCTING A PELVISCOPY

The present invention relates to a bipolar forceps for pelviscopy permitting coagulation of tissues.

There are known forceps of this type which are of two parallel metallic blades connected to a voltage source to use the blades as electrodes.

The forceps comprises means for moving the blades relative to each other, when the latter is introduced into a cannula or trocar to deform the free ends of each blade so as to grip the tissues to be coagulated.

The displacement means are generally constituted by two handles of which one is moveable to prevent sliding the blades within the cannula or trocar so as to deform the ends.

It is noted that the blades have an external diameter of about 5 millimeters, which is too large to penetrate the guides or cannulae of smaller diameter, which are provided between 1.5 and 3 millimeters internal diameter.

Also, it is noted that the metallic material used for the construction of the blades, such as an alloy, does not permit reducing the external diameter of the forceps without risking impeding its operation.

It is these drawbacks that the present invention seeks more particularly to overcome.

The bipolar forceps according to the present invention has for its object to be able to be introduced into the interior of guides or cannulae whose internal diameter is less than 5 millimeters, whilst guaranteeing a perfect operation of the blades during their resilient deformation.

The bipolar forceps according to the present invention comprises a pair of blades covered with an insulating sheath, a guide for the sliding of the pair of blades, a voltage source connected to each blade so that the latter operates as an electrode to permit the coagulation of tissues, a pair of blades made of an alloy having shape memory, which are partially covered with a sheath of plastic material so as to be fixed within a tube, whilst each blade has an unsheathed end with a curved cross section forming jaws which are held in deformed position within the guide, which is to say in a closed position by means of resilient return means, and a cylindrical support, within which is disposed the pair of blades secured to the tube, said cylindrical support comprising, opposite resilient return means, connection means which permit securement of the bipolar forceps on the guide.

The bipolar forceps according to the invention comprises resilient return means which are constituted by a handle and a return spring disposed in the internal portion of the cylindrical support to come into bearing against an abutment of the cylindrical tube.

The bipolar forceps according to the present invention comprises blades which are made of an alloy with shape memory of the hyper-elastic type, to be able to have a very small external diameter and a large deformation of the ends.

The bipolar forceps according to the present invention comprises blades which have a long length of the sheathed portion, an oblong profile of constant thickness.

The bipolar forceps according to the present invention comprises blades whose unsheathed ends of the blades have an oblong profile whose thickness is less than that of the sheathed portion, permitting better resilient deformation under external force on the one hand, and a greater contact surface facilitating the coagulation of the tissues on the other hand.

The bipolar forceps according to the present invention comprises blades which are interconnected by means of a cylindrical tube which has at each end circular deformations permitting the longitudinal blockage of the blades between themselves.

The bipolar forceps according to the present invention comprises blades which are surrounded by other sleeve over all the length of the first sleeve, permitting their securement together so as to prevent them from moving longitudinally relative to each other.

The bipolar forceps according to the present invention comprises a cylindrical support comprising, adjacent the connection means, a sealed connection of the valve type for the introduction of a fluid into the internal channel of the guide and into the operating site.

The bipolar forceps according to the present invention comprises a cylindrical support comprising resilient return means which are constituted by a handle formed by a curved and flexible branch which comes to bear against a casing of the voltage source.

The bipolar forceps according to the present invention comprises a cylindrical support comprising, opposite the handle secured to its branch, a sealed connection of the valve type to introduce a fluid into the internal channel of the guide and into the operating site.

The description which follows with respect to the accompanying drawings, given by way of nonlimiting example, permits better understanding of the invention, the characteristics which it provides, and the advantages which it is adapted to supply:

FIGS. 1 and 2 are views showing the bipolar forceps for pelviscopy according to the present invention.

There is shown in FIGS. 1 to 4 a bipolar forceps 1 for pelviscopy, comprising a pair of blades 2 which are connected to a voltage source 3, such that each blade functions as an electrode for the coagulation of tissues.

Each blade 2 is made of an alloy with shape memory of the hyper-elastic type, to be able to have a very small external diameter, of the order of 1.6 millimeters, and an important deformation of the ends of said blades.

Figure 3:
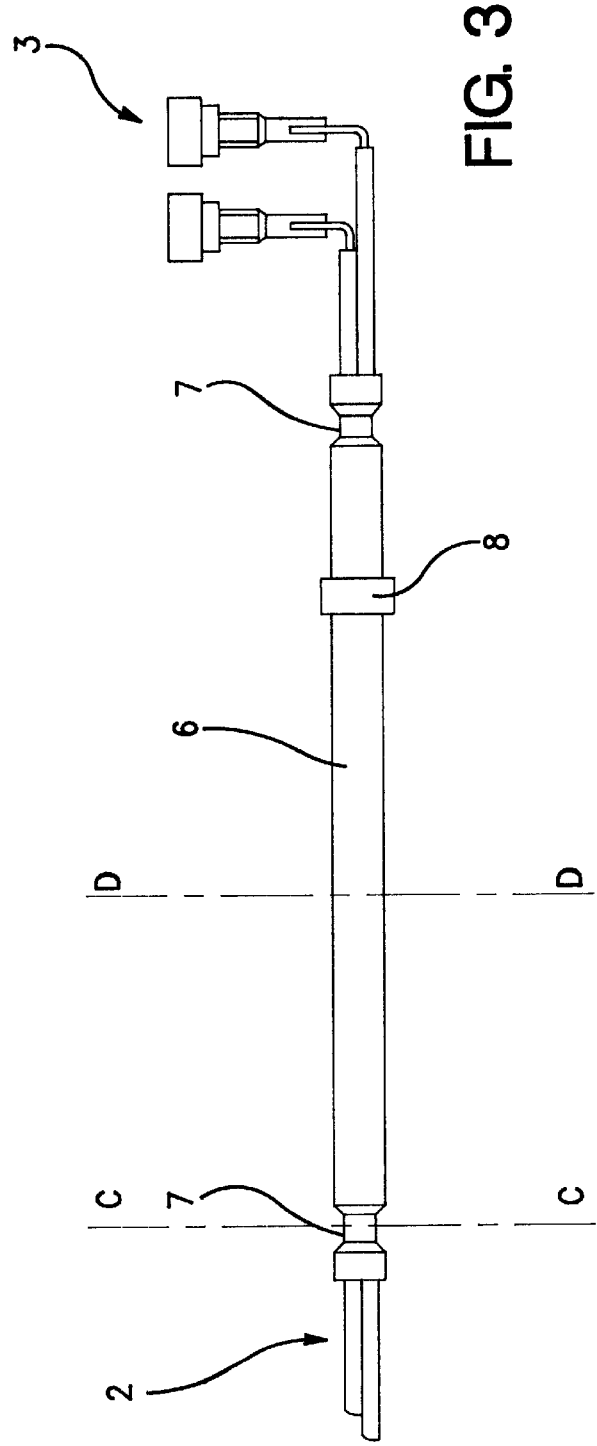
FIGS. 3 and 4 are detailed views showing the arrangement of the hyper-elastic blades of the forceps for pelviscopy, according to the present invention.
Figure 4:
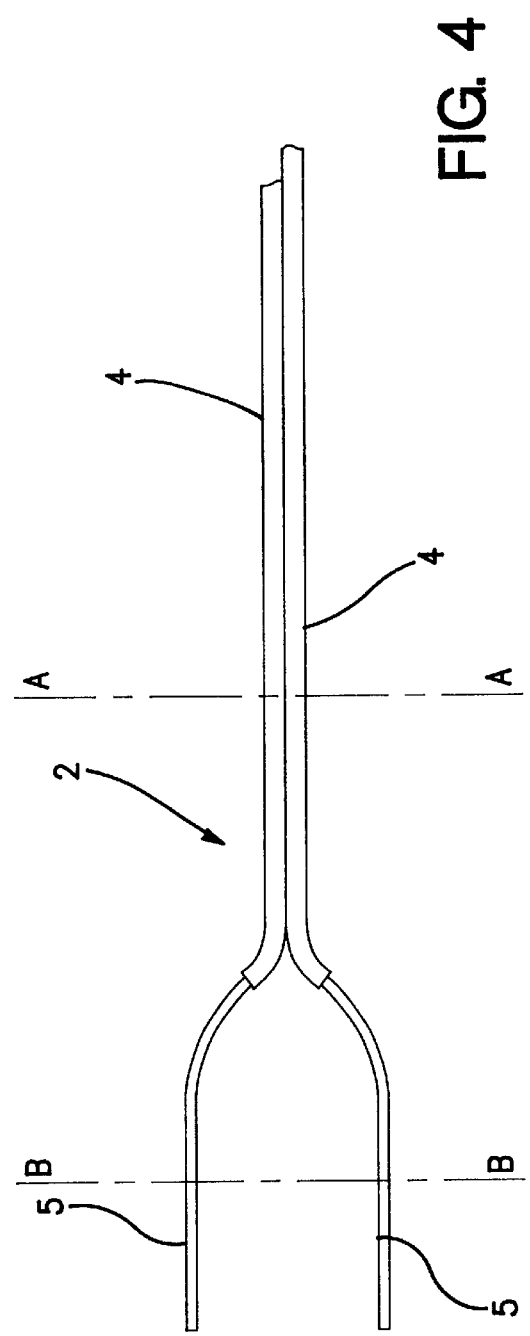
Figure 5A:
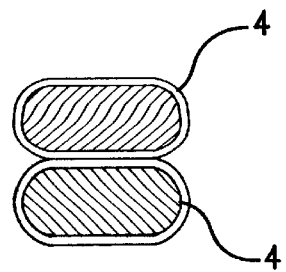
FIG. 5a is a cross section on the line AA of FIG. 4, showing the sheathing of the hyper-elastic blades of the forceps for pelviscopy according to the present invention.
Figure 5B:
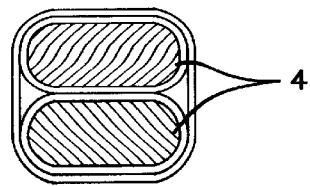
FIG. 5b is a cross section similar to that of FIG. 5a showing a modified sheathing of the hyper-elastic blades of the forceps for pelviscopy according to the present invention.

The blades 2 are partially covered with a sleeve 4 of plastic material permitting insulating them from each other over a large portion of the latter. It will be seen that the blades 2 have over the length of the sleeve portion 4 an oblong profile of constant thickness (FIGS. 5a, 5b).

Figure 5C:
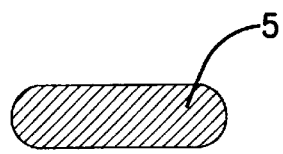
FIG. 5c is a cross section on the line BB of FIG. 4, showing the cross section of the unsheathed end of the hyper-elastic blades of the forceps for pelviscopy according to the present invention.

The blades 2 each comprise one end 5, unsheathed, constituting the jaws of the bipolar forceps 1. It will be noted that the ends 5 of the blades 2 have an oblong cross sectional shape whose thickness is less than that provided for the sleeved portion 4 (FIG. 5c). The thinner profile of the ends 5 of each blade 2 permits a better resilient deformation under external force, on the one hand, and a greater contact surface facilitating coagulation of the tissues, on the other hand.

Figure 5D:
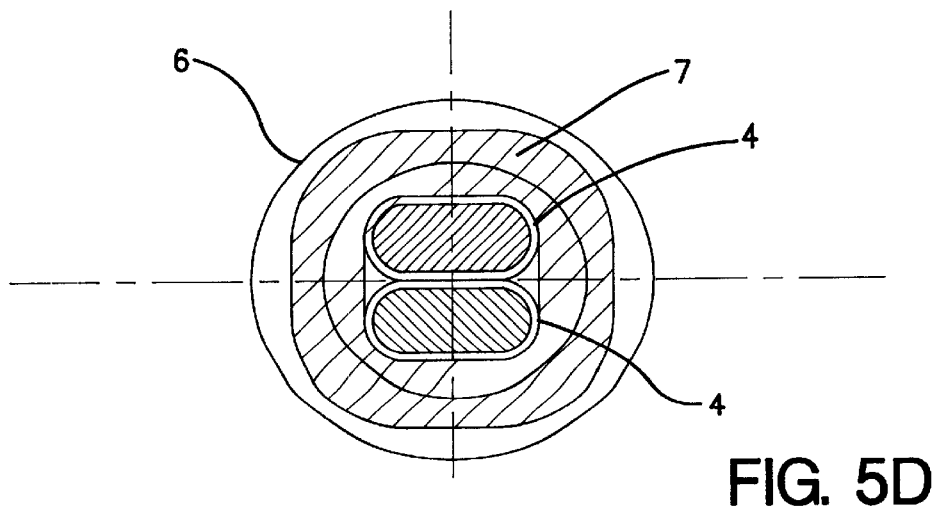
FIG. 5d is a cross section on the line CC of FIG. 3, showing the securement of the hyper-elastic blades within the tube of the forceps for pelviscopy according to the present invention.
Figure 5E:
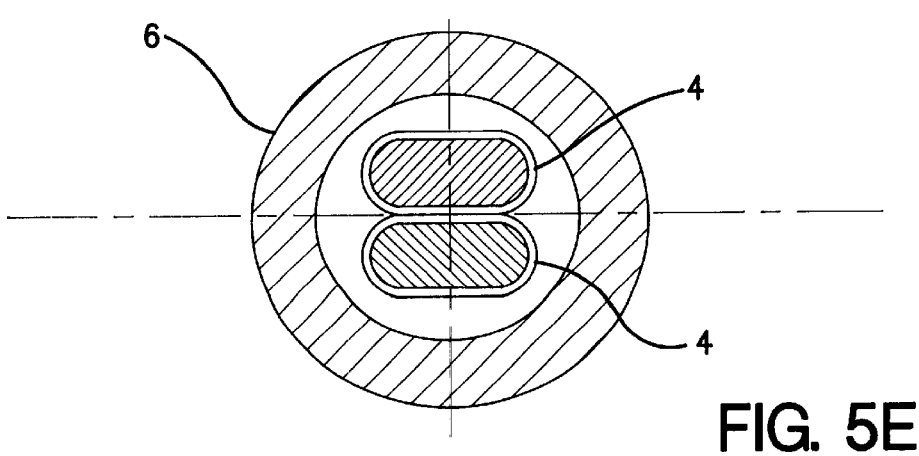
FIG. 5e is a cross section on the line DD of FIG. 3, showing the passage of the hyper-elastic blades within the tube of the forceps for pelviscopy according to the present invention.

The blades 2 are interconnected by means of a cylindrical tube 6 which has at each end circular deformations 7 permitting longitudinal blocking of the blades together and avoiding the blades moving relative to each other. The tube 6 comprises on its periphery, and adjacent to deformation 7, a circular abutment 8 permitting limiting the longitudinal path of the blades 2 (FIGS. 5d, 5e).

Prior to securement of the blades 2 together within the tube 6, the latter can be surrounded by another sleeve 9 over all the length of the first sleeve 4. The sleeve 9 can also replace the tube 6, because the wrapping of this latter about the blades 2 permits the securement together so as to prevent them from moving longitudinally relative to each other (FIG. 5b).

The tube 6 and the blades 2 are disposed within a cylindrical support 10 comprising at one end, and more particularly the end turned toward the sides of the jaws 5, connection means 11 which permit the securement of the forceps 1 on a small diameter guide 12.

The cylindrical support 10 comprises, opposite the end carrying the connection means 11, resilient return means 13 which are constituted by a handle 14 and a return spring (not shown) but disposed in the internal portion of said support to come into bearing against the abutment 8 of the cylindrical tube 6.

It will be noted that the forceps 1 has, before any introduction into a guide of small diameter 12, jaws 5 which are always in open position because of the curved profile which has been given to the blades 2.

Figure 6A:
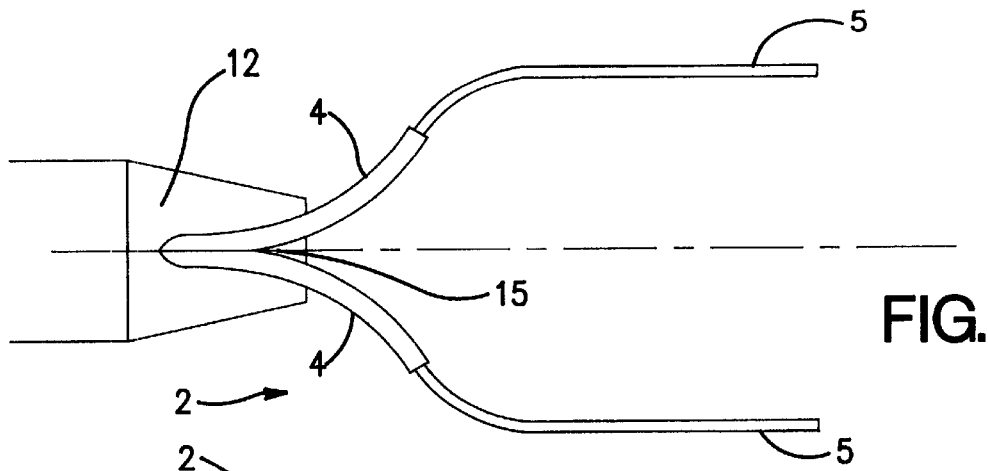
FIGS. 6a to 6e are fragmentary views showing the maximum path for deformation of the hyper-elastic blades within the guide of small diameter.
Figure 6B:
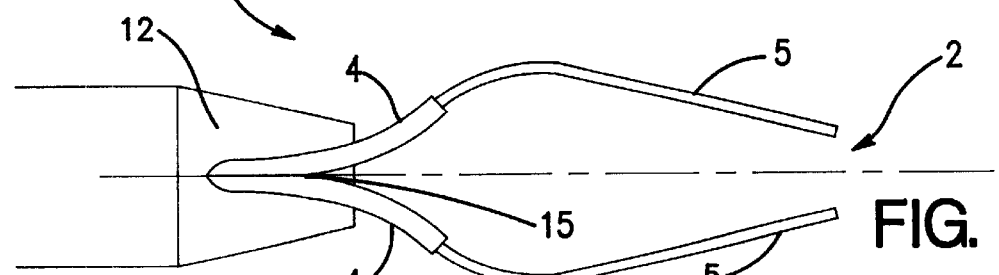
Figure 6C:
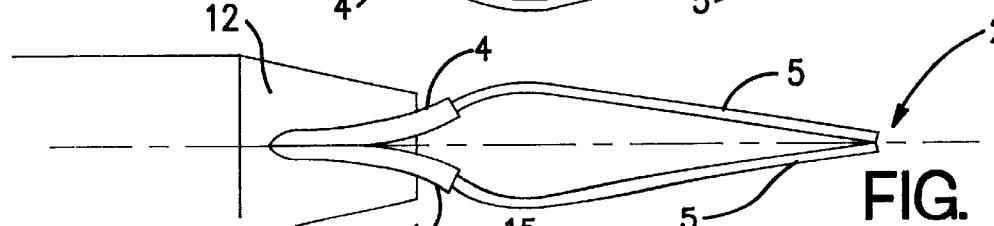
Figure 6D:
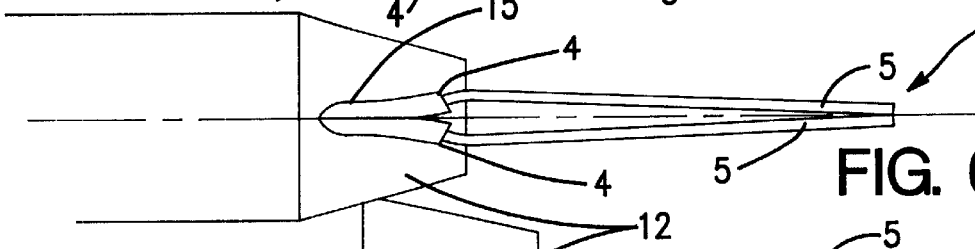
Figure 6E:
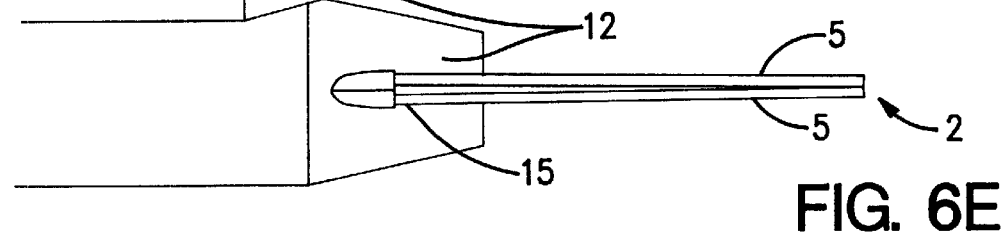

When the forceps 1 is introduced into the guide 12, and locked on this latter by means of connection means 11 of the cylindrical support 10, it will be noted that the resilient return means 13 hold relative to the free end of said guide the jaws 5 of the blades 2 against each other, which is to say in a closed position (FIG. 6e).

Thus, the resilient return means 13 determine the maximum longitudinal path which the blades 2 can follow within the support 10 and the guide 12.

The closed position, the so-called rest position of the blades 2, is obtained by the fact that these latter penetrate sufficiently within an internal channel 15 of the guide 12 to deform the curved profile of the jaws 5 and to apply them against each other.

There would be understood by rest position, the position of the forceps 1 introduced into the operating site by means of the guide 12 of small diameter and before any use of said forceps by the surgeon.

When the surgeon wants to open the jaws 5 of the blades 2 of the forceps 1, he need only take between his fingers of one of his hands the handle 14 of the support 10 and push on the casing 16 of the voltage source 3, whilst the other hand retains the guide 12 such that the blades 2 leave the internal channel 15 and open because of their resilient characteristics of shape memory.

The longitudinal movement of the casing 16 in the direction of the support 10 permits sliding the blades 2 within said support and guide 12 so as to free the jaws 5 from the internal channel 15 (FIG. 6a).

The surgeon can position between the open jaws 5 of the blades 2, tissues to be cauterized, such as blood vessels or the like.

The surgeon progressively releases the housing 16 so that the resilient return means 13 move the blades 2 longitudinally relative to the guide 12 and within the channel 15 to close the jaws 5 about the tissue to be cauterized (FIGS. 6b to 6e).

It then suffices to apply at the level of the jaws 5 an alternating voltage of the high frequency type by means of the voltage source 3, so as to cauterize or coagulate the tissue.

The surgeon proceeds to open the jaws 5 to free the cauterized tissue by pushing again on the casing 16 so that the blades 2 slide within the guide 12 (FIG. 6a).

Figure 7:
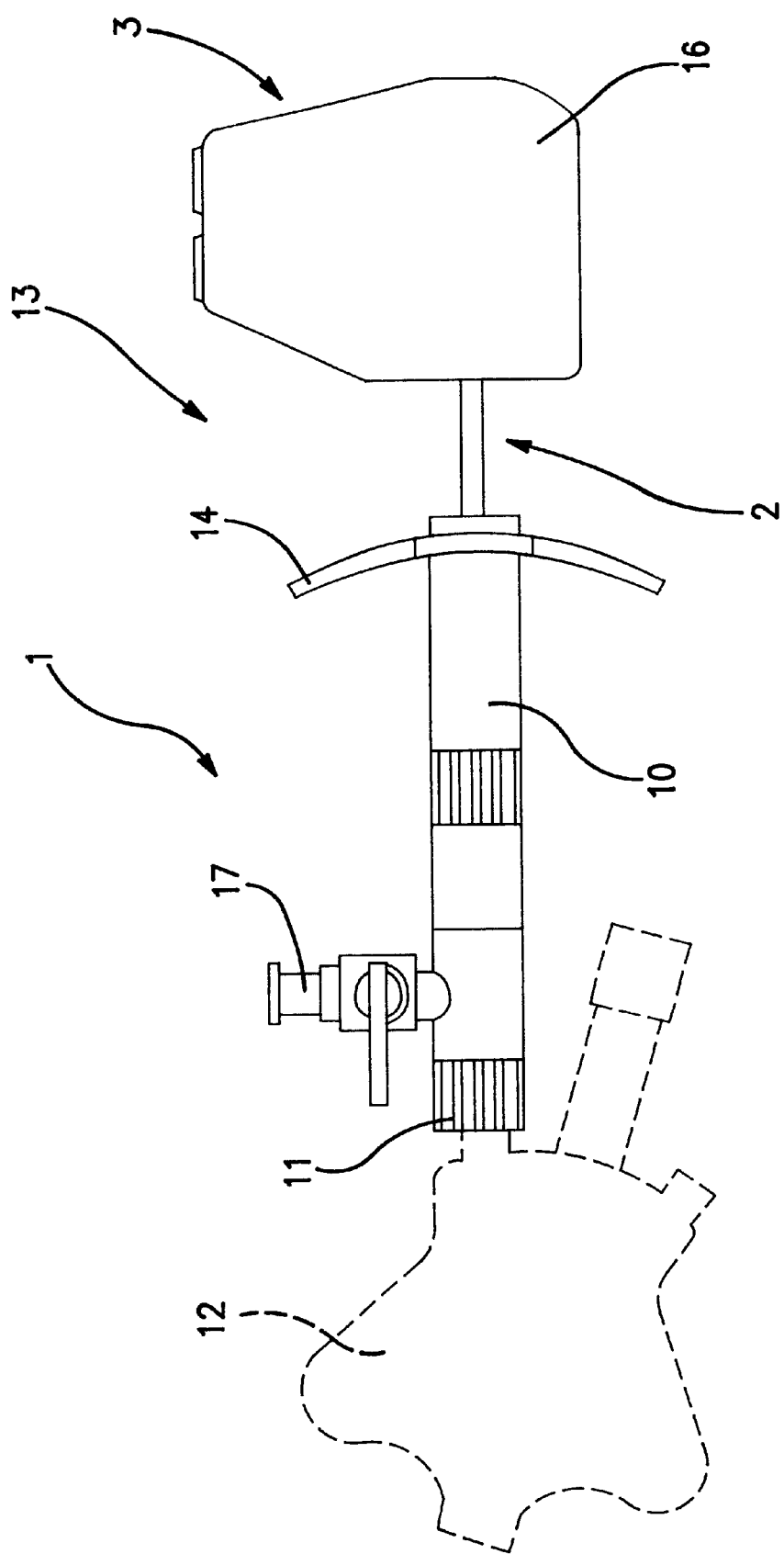
FIG. 7 is a view showing the cylindrical support of FIG. 1 provided with fluid supply means for the internal channel of the guide receiving the forceps for pelviscopy according to the present invention.

In FIG. 7 is shown a first modification of the support 10 of FIG. 1 as to the emplacement adjacent the connection means 11 of a sealed connection 17 of the valve type to introduce into the internal channel 15 of the guide 12 and into the operating site a fluid.

Figure 8:
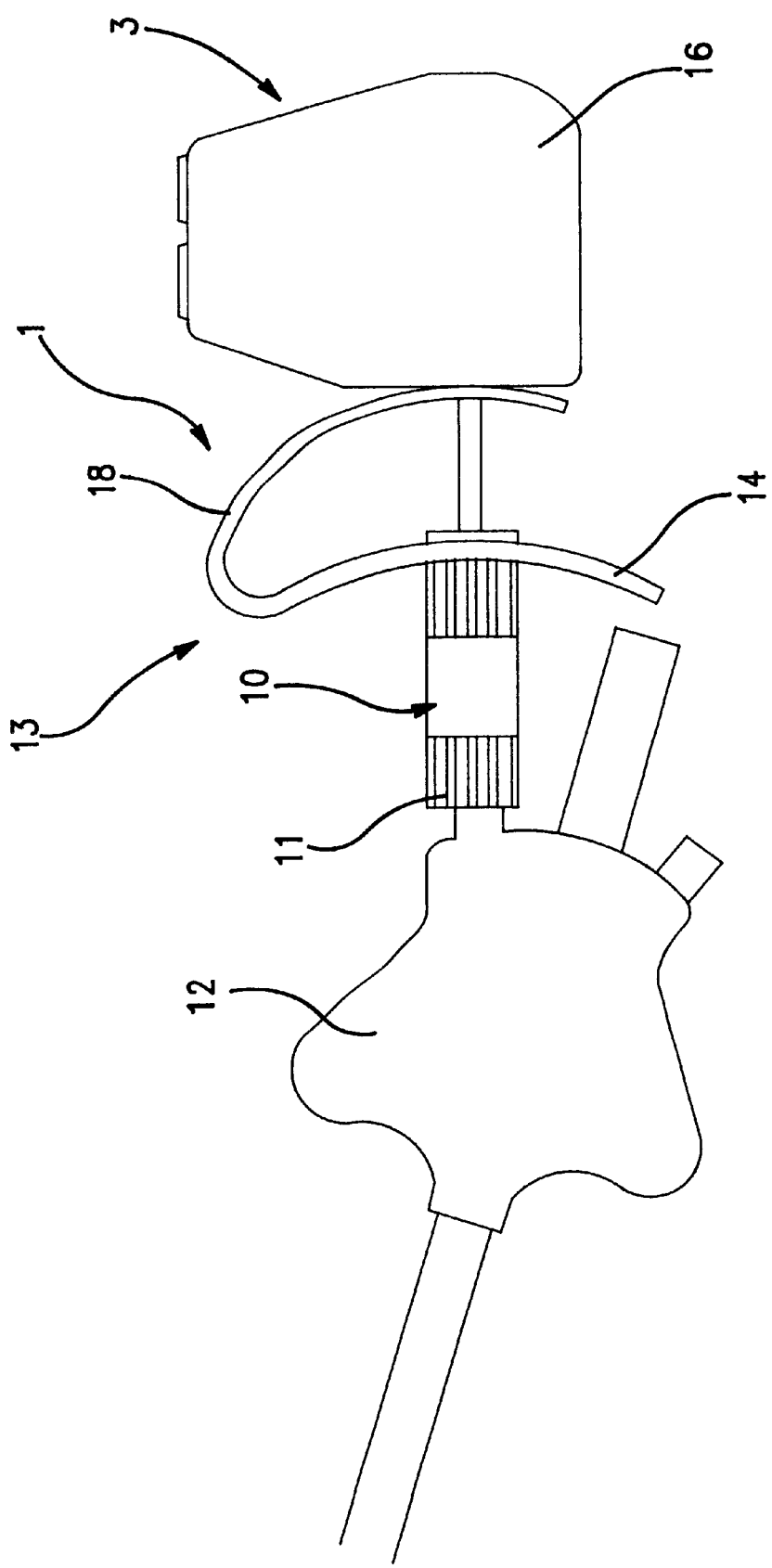
FIG. 8 is a view showing a modification of the cylindrical support and more particularly of the resilient return means of the forceps for pelviscopy according to the present invention.

In FIG. 8 is shown a second modification of the support 10 of FIG. 1, as to the resilient return means 13 which are constituted by a handle 14 formed of a curved and flexible branch 18 which bears against the casing 16 of the voltage source 3.

The branch 18 permits replacing the spring introduced within the support 10 and which bears against the abutment 8 of the cylindrical tube 6.

Figure 9:
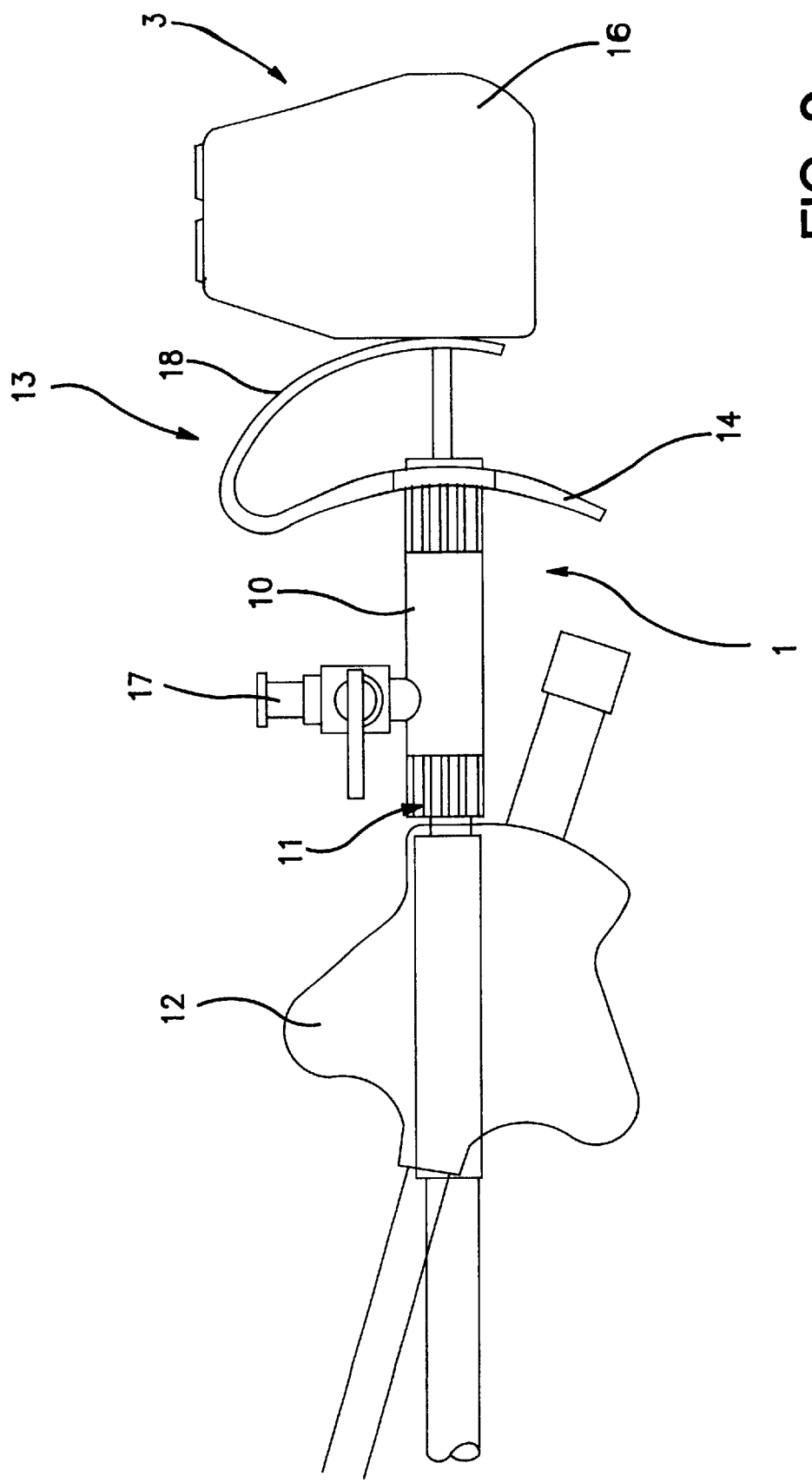
FIG. 9 is a view showing a modified cylindrical support of FIG. 8 on which are provided supply means for the internal channel of the guide receiving the forceps for pelviscopy according to the present invention.

In FIG. 9 is shown a modification of the support 10 of FIG. 8, which consists in providing, opposite the handle 14 secured to the branch 18, a sealed connection 17 of the valve type for the introduction into the internal channel 15 and into the operating site a fluid.

It will be noted that the resilient return means can operate reversely than has been described above without thereby changing the object of the invention.

It will be noted that the guide 12 on which the support 10 of the forceps 1 is fixed, can be, for example, the universal catheter described in French patent application FR 97 13988 belonging to the applicants.

The use of the universal catheter as the guide 12, permits the surgeon to perform a particular operation connected with fertilization by coagulation of the tubes.

It should moreover be understood that the preceding description is given only by way of example and in no way limits the scope of the invention, from which one would not depart by replacing the details of execution described, by all other equivalents.

What is claimed is:

1. Bipolar forceps for pelviscopy permitting the coagulation of tissues, comprising a pair of blades (2) covered with an insulating sheath (4), a guide (12) for the sliding of the pair of blades (2) and a source of voltage (3) connected to each blade (2) so that these latter operate as electrodes to permit the coagulation of tissues, wherein:

the pair of blades (2) are made of an alloy with shape memory, which are partially covered with the insulating sheath (4) of plastic material so as to be fixed within a tube (6), whilst each blade (2) has an unsheathed end (5) with a curved cross section forming jaws which are held in a deformed position within the guide (12), which is to say, in a closed position by means of a resilient return means (13), and a cylindrical support (10), within which is disposed the pair of blades (2) secured to the tube (6), said cylindrical support comprising, opposite the elastic return means (13), connection means (11) which permit the securement of the bipolar forceps (1) on the guide (12).

2. Bipolar forceps according to claim 1, characterized in that the resilient return means (13) are constituted by a handle (14) and a return spring disposed in the internal portion of the cylindrical support (10) to come into engagement against an abutment (8) of the cylindrical tube (6).

3. Bipolar forceps according to claim 1, characterized in that each blade (2) is made of an alloy with shape memory of the hyper-elastic type to be able to have a very small external diameter and a large deformation of the ends (5).

4. Bipolar forceps according to claim 2, characterized in that the blades (2) have over the length of the sheathed portion (4) an oblong cross section of constant thickness.

5. Bipolar forceps according to claim 1, characterized in that the unsheathed ends (5) of the blades (2) have an oblong cross section whose thickness is less than that of the sheathed portion (4) permitting a better resilient deformation under external force on the one hand, and a larger contact surface facilitating coagulation of the tissues on the other hand.

* * * * *